United States Patent
Kurita et al.

(10) Patent No.: US 9,988,672 B2
(45) Date of Patent: Jun. 5, 2018

(54) METHYLCYTOSINE DETECTION METHOD

(71) Applicant: NATIONAL INSTITUTE OF ADVANCED INDUSTRIAL SCIENCE AND TECHNOLOGY, Tokyo (JP)

(72) Inventors: Ryoji Kurita, Tsukuba (JP); Hiroyuki Yanagisawa, Tsukuba (JP); Kyoko Yoshioka, Tsukuba (JP); Osamu Niwa, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 113 days.

(21) Appl. No.: 14/775,004

(22) PCT Filed: Mar. 13, 2014

(86) PCT No.: PCT/JP2014/056633
§ 371 (c)(1),
(2) Date: Dec. 9, 2015

(87) PCT Pub. No.: WO2014/142228
PCT Pub. Date: Sep. 18, 2014

(65) Prior Publication Data
US 2016/0138080 A1    May 19, 2016

(30) Foreign Application Priority Data
Mar. 14, 2013  (JP) .................... 2013-051501

(51) Int. Cl.
*C12Q 1/6804* (2018.01)
*C12Q 1/68* (2018.01)
*G01N 33/53* (2006.01)

(52) U.S. Cl.
CPC .......... *C12Q 1/683* (2013.01); *C12Q 1/6804* (2013.01); *C12Q 1/6827* (2013.01); *G01N 33/5308* (2013.01); *G01N 2440/12* (2013.01)

(58) Field of Classification Search
None
See application file for complete search history.

(56) References Cited

U.S. PATENT DOCUMENTS

| 5,804,384 A * | 9/1998 | Muller | ................ | C12Q 1/6837 435/287.2 |
| 2011/0189674 A1* | 8/2011 | Tomigahara | ......... | C12Q 1/6804 435/6.11 |

FOREIGN PATENT DOCUMENTS

| JP | 2004-008217 | 1/2004 |
| JP | 2006-238701 | 9/2006 |

(Continued)

OTHER PUBLICATIONS

Campbell et al. Journal of Chromatography. 2009. 877:4079-4089. (Year: 2009).*

(Continued)

*Primary Examiner* — Joseph G. Dauner
(74) *Attorney, Agent, or Firm* — Myers Bigel, P.A.

(57) ABSTRACT

To provide a method for selectively detecting the methylation of particular cytosines in genomic DNA using a methylcytosine detection method using an anti-methylcytosine antibody to improve quantitativity and reliability. A method for detecting the methylated state of cytosine at a specific position contained in a nucleic acid, includes fragmenting the nucleic acid using a restriction enzyme; forming a double-stranded nucleic acid between the fragmented nucleic acid and a single-stranded nucleic acid having a base sequence capable of hybridizing with the fragmented nucleic acid but incapable of resulting in the formation of a base pair with cytosine at a specific position in the fragmented nucleic (Continued)

acid and a solid phase-binding site; binding the double-stranded nucleic acid on a solid phase using the solid phase-binding site; and measuring the amount of an antibody binding to the double-stranded nucleic acid on the solid phase.

9 Claims, 6 Drawing Sheets

(56) References Cited

FOREIGN PATENT DOCUMENTS

| JP | 3854943 B2 | 12/2006 |
| JP | 2010-048566 | 3/2010 |
| JP | 2012-230019 | 11/2012 |
| WO | WO 2005/080565 A1 | 9/2005 |

OTHER PUBLICATIONS

Vashist et al. Procedia Chemistry. 2012. 6:184-193. (Year: 2012).*
Arlett et al. Nature Biotechnology. 2011. 6:203-215. (Year: 2011).*
Cho et al. J Vet Med Sci. 2006. 68(12):1327-1329. (Year: 2006).*
Cho et al. J Vet Diagn Invest. 2007. 19:414-416. (Year: 2007).*
Lofgren et al. The Journal of Immunology. 2007. 178:7467-7472. (Year: 2007).*
Kurita et al. "DNA Methylation Analysis Triggered by Bulge Specific Immuno-Recognition", *Anal. Chem.* 84:7533-7538 (2012).
Kurita et al. "DNA Bulge Tokuiteki na Kotai Ninshiki 0 Riyo shita Cytosine no Methylka Shindan", The Japan Society for Analytical Chemistry Dai 61 Nenkai Koen Yoshishu, 2012, p. 51.
Kurita et al. "DNA Bulge nl Haichi sareta Methyl Cytosine to Kotaikan deno Sogo Sayo Kaiseki", Dai 73 Kai Abstracts of the Symposium of the Japan Society for Analytical Chemistry, May 2013, p. 10.
Kurita et al. "NA Bulge o Riyo shita Ichi Sentakuteki Methyl Cytosine Keisoku Chip no Kaihatsu", Society for Chemistry and MicroNano Systems Dai 27 Kai Kenkyukai Koen Yoshishu, May 2013, p. 17.
International Search Report corresponding to International Application No. PCT/JP2014/056633 dated Jun. 17, 2014.
Office Action corresponding to Japanese Application No. 2013-051501 dated Oct. 4, 2016.

* cited by examiner

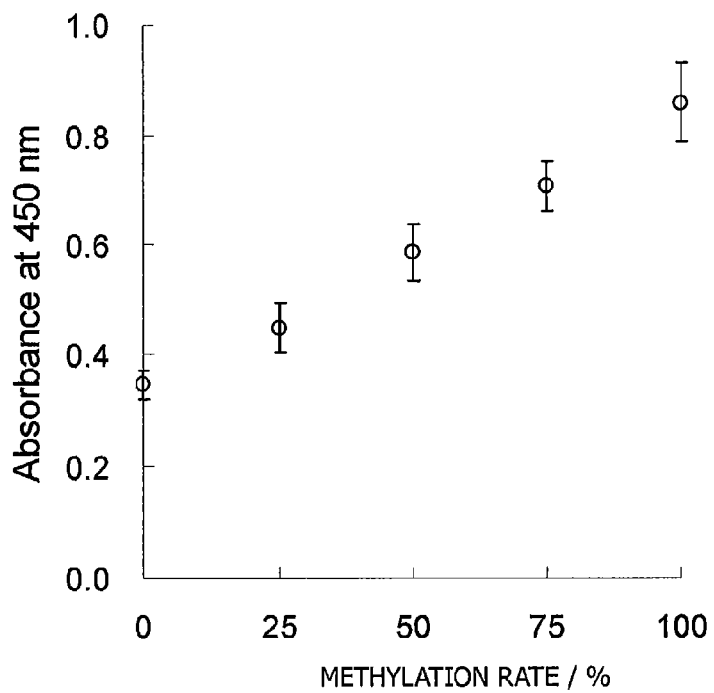
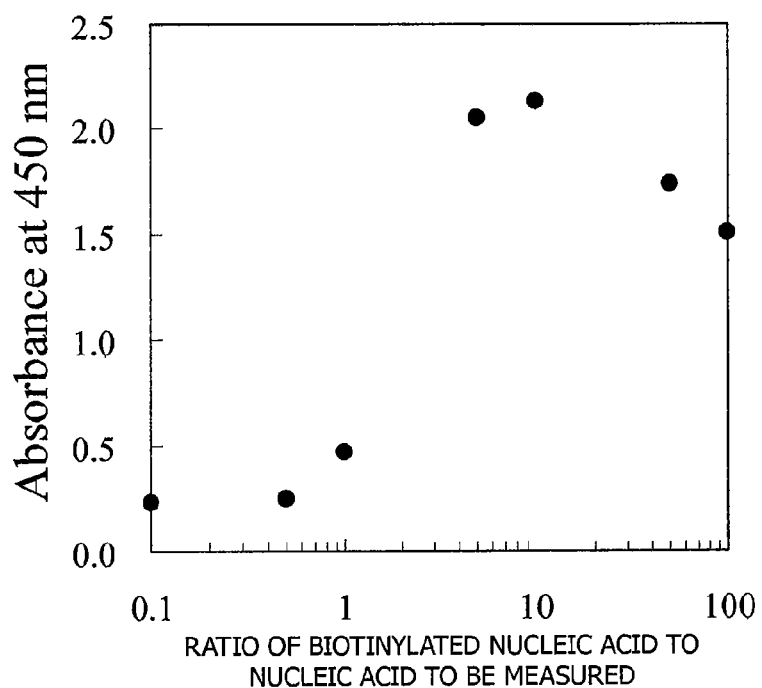

METHYLCYTOSINE DETECTION METHOD

RELATED APPLICATIONS

This application is a 35 U.S.C. § 371 national phase application of PCT Application PCT/JP2014/056633 filed Mar. 13, 2014 which claims priority to Japanese Application No. 2013-051501 filed Mar. 14, 2013. The entire contents of each are incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 5576-304TS_ST25.txt, 2,392 bytes in size, generated on Sep. 8, 2015 and filed via EFS-Web, is provided in lieu of a paper copy. This Sequence Listing is incorporated by reference into the specification for its disclosures.

TECHNICAL FIELD

The present invention relates to a biomolecular detection method for detecting the methylated state of cytosine at a specific position in a nucleic acid.

BACKGROUND ART

It is becoming evident that methylation of the genome is an example of epigenetics observed in a wide range of biological species from *Escherichia coli* to plants to vertebrates, and this is associated with various living phenomena. Particularly in mammals, the methylation is also becoming an important area of study in view of ontogenesis, cell differentiation, canceration, and the like, and methylation of CpG islands in the promoter region of a gene is known to inactivate tumor-suppressor genes.

The methylation of a genome specifically arises from the methylation of cytosine contained in nucleic acid. The bisulfite method is currently most widely used as a method for detecting the methylated state of the cytosine contained in nucleic acid is a method utilizing the fact that bisulfite treatment of nucleic acid as a specimen does not convert methylcytosine and converts only cytosine to uracil (Patent Literatures 1 and 2). When after bisulfite treatment, the resultant is subjected to PCR and sequenced, uracil is detected as thymine and methylcytosine is detected as cytosine. The presence or position of methylation can be determined from the difference between cytosine and thymine (uracil) produced before and after treatment. However, the disadvantages of the bisulfite method are that its sequencing operation is cumbersome, the method has a long reaction time (typically a dozen hours or so) for complete modification, and the treatment often produces a depurination reaction and often causes fragmentation of the sample; thus, the method requires improvement.

As a method other than this method, a quantitation method for methylcytosine using an anti-methylcytosine antibody has been reported (Patent Literature 3). However, the quantitation method for methylcytosine using the antibody can measure the total amount of methylcytosine contained in a nucleic acid of interest, but does not enable it to be determined at which position in the base sequence cytosine is methylated. For gene expression, it is crucial to know which cytosines are methylated, not just the frequency of cytosine methylation.

The present inventors have recently reported a method for selectively quantitating the methylation of cytosine at a specific position in a base sequence using an anti-methylcytosine antibody together with experimental results using synthetic oligomers (Patent Literature 4). This method involves placing the cytosine to be detected at a specific position in a nucleic acid in a DNA bulge formed by mismatching when the nucleic acid hybridizes with a complementary strand and measuring the amount of an anti-cytosine antibody or an anti-methylcytosine antibody binding to the nucleic acid; this enables it to be determined whether or not the cytosine to be detected is methylated.

CITATION LIST

Patent Literature

Patent Literature 1: Japanese Patent Application Laid-Open No. 2006-238701
Patent Literature 2: Japanese Patent Application Laid-Open No. 2004-008217
Patent Literature 3: Japanese Patent No. 3854943
Patent Literature 4: Japanese Patent Application Laid-Open No. 2012-230019

SUMMARY OF INVENTION

Technical Problem

The method for determining whether or not the particular cytosine to be detected in a nucleic acid is methylated by placing the cytosine to be detected in a DNA bulge formed when the nucleic acid hybridizes to a complementary strand and measuring the amount of an antibody binding to the nucleic acid can advantageously detect the methylation of the cytosine in experiments using synthesized oligomers, but it is difficult for a method like this to detect the methylation of a particular cytosine when the genomic DNA to actually be analyzed is used. This is because the presence of a large amount of DNA other than the base sequence of interest makes it difficult to selectively detect only methylated cytosine at a specific site since methylated cytosine can be present in areas other than that hybridizing to a complementary strand and the antibody also binds to the methylated cytosine.

An object of the present invention is to eliminate the drawback of the invention and to provide a method for selectively detecting the methylation of particular cytosines in genomic DNA using a methylcytosine detection method using an anti-methylcytosine antibody to improve quantitativity and reliability.

Solution to Problem

The present inventors have succeeded in selectively detecting methylation of particular cytosines in genomic DNA, as explained below.

A restriction enzyme was first added to the genomic DNA specimen to be measured, to fragment the DNA. The nucleic acid sequence of each of the formed DNA fragments is dependent on the restriction enzyme used. This enables the excision, from the genome, of the nucleic acid to be measured consisting of a particular sequence containing the cytosine to be detected at a specific position as its fragment.

An ultrasonic wave or the like has conventionally been used to fragment DNA; however, such a method produces a variable number of fragments and thus is not suitable for the methylcytosine detection method of the present invention using a nucleic acid having complementarity to the nucleic acid to be measured as a detection reagent, as will be described below, although this does not present a particular problem in a subsequent PCR method or the like for amplifying the particular sequence.

The nucleic acid to be measured has then been mixed with a single-stranded nucleic acid having a sequence complementary to the nucleic acid to be measured except for a base with which the cytosine to be detected is to form a base pair for hybridization to form a double-stranded DNA.

The base sequence of the single-stranded nucleic acid is a sequence not forming a base pair with the cytosine to be detected while having complementarity and length sufficient to form a double strand with the nucleic acid to be measured. The base sequence is designed considering the end sequence of the nucleic acid to be measured formed by cleavage with the restriction enzyme so that an unpaired base is not left at the end of the formed double-stranded DNA.

The formed double-stranded DNA is subsequently bound to a solid phase via a solid phase-binding site provided in the single-stranded nucleic acid for recovery on the solid phase. The remaining DNA fragments are removed by washing.

Thereafter, the double-stranded DNA bound on the solid phase is exposed to an antibody.

Even when the formation of a double strand with the complementary nucleic acid has resulted in the presence of methylcytosine at a position that is not determined in the nucleic acid to be analyzed, the methylcytosine forms a base pair with guanine so as to greatly decrease the probability of being recognized by the antibody. In contrast, methylcytosine at the position to be determined, not forming the base pair is recognized by a highly efficient antigen-antibody reaction. This has enabled the selective detection of the methylated states of particular cytosines in genomic DNA.

Further details of the steps of the present invention follow.

(1) A nucleic acid to be measured is cleaved and fragmented with a restriction enzyme.

Although various restriction enzymes recognizing a particular base sequence and cleaving a nucleic acid are known, a restriction enzyme can be selected, which is capable of cleaving the base sequence to be measured in a manner flanking the sequence. One restriction enzyme may be used, or a combination of two restriction enzymes may be used.

(2) Hybridization is performed by adding a single-stranded nucleic acid having a base sequence designed so that the cytosine to be detected does not form a base pair while forming a double strand with the base sequence of interest.

Genomic DNA typically forms a double strand in vivo. Thus, the fragmented nucleic acid is preferably once heated to or above its melting temperature after adding the single-stranded nucleic acid to make single strands and again slowly cooled for hybridization with the single-stranded nucleic acid. In addition, it is preferable to add the single-stranded nucleic acid in excess based on the nucleic acid to be measured to highly efficiently hybridize with the single-stranded nucleic acid. Further, the base sequence of the single-stranded nucleic acid is designed considering a combination with the restriction enzyme so that an unpaired base does not remain at the end of the formed double-stranded DNA. It is ensured that the single-stranded nucleic acid also has a solid phase-binding site for subsequent recovery on the solid phase.

(3) The double-stranded nucleic acid having the solid phase-binding site hybridized to the object to be measured is recovered utilizing the solid phase-binding site.

In recovery, it is a good idea to provide a solid phase suited for a subsequent detection method. For example, recovery on a gold or silver thin film is desirable for a surface plasmon resonance method. Recovery may also be performed in wells of a microtiter plate, followed by detection using an enzyme immunoassay method. Recovery may be performed not only on a flat material such as a substrate, but also on polystyrene or magnetic particles.

(4) An antibody is introduced, and the amount of the bound antibody is measured to measure the rate of cytosine methylation.

For example, when an anti-methylcytosine antibody is added, the methylation of the cytosine to be detected will result in the binding of the anti-methylcytosine antibody to the double-stranded nucleic acid. The surface plasmon resonance method can detect the antibody from a change in a refractive index without labeling the antibody with an enzyme or a fluorophore. Common techniques having been used for conventional immunoassay methods can be widely used. As is obvious to one skilled in the art, there is, for example, a method which involves labeling the antibody with an enzyme, a fluorophore, a radioisotope, or a metallic nanoparticle. Detection by introducing a secondary antibody labeled with any of the labels is also possible.

Thus, the invention of the present application has the following aspects.

1. A method for detecting the methylated state of cytosine at a specific position in a nucleic acid, comprising the steps of:

fragmenting the nucleic acid using a restriction enzyme;

forming a double-stranded nucleic acid between the fragmented nucleic acid and a single-stranded nucleic acid having a base sequence capable of hybridizing with the fragmented nucleic acid but incapable of resulting in the formation of a base pair with cytosine at a specific position in the fragmented nucleic acid and a solid phase-binding site;

binding the double-stranded nucleic acid on a solid phase using the solid phase-binding site; and measuring the amount of an antibody binding to the double-stranded nucleic acid on the solid phase.

2. The method according to 1, wherein the antibody is an anti-methylcytosine antibody.

3. The method according to 1 or 2, wherein the solid phase-binding site is biotin and the solid phase is avidin.

4. The method according to any one of 1 to 3, wherein the amount of the antibody binding to the double-stranded nucleic acid is measured by detecting the binding of the antibody by a surface plasmon resonance method.

5. The method according to 1 to 3, wherein the amount of the antibody binding to the double-stranded nucleic acid is measured by using a horseradish peroxidase-labeled antibody as the antibody, binding the antibody before adding a substrate for the horseradish peroxidase, and detecting a change in absorbance due to a reaction product of the horseradish peroxidase.

6. The method according to 1 to 5, wherein the base sequence capable of hybridizing to the fragmented nucleic acid but incapable of resulting in the formation of a base pair with cytosine at a specific position in the fragmented nucleic acid used is a single-stranded nucleic acid having a base sequence in which the point to form a base pair with the cytosine to be detected is an abasic site.

7. The method according to 1 to 5, wherein the base sequence capable of hybridizing to the fragmented nucleic acid but incapable of resulting in the formation of a base pair with cytosine at a specific position in the fragmented nucleic acid used is a single-stranded nucleic acid having a base sequence in which the cytosine to be detected is to be placed in a bulge structure in forming the double-stranded nucleic acid.

8. The method according to 1 to 5, wherein the base sequence capable of hybridizing to the fragmented nucleic acid but incapable of resulting in the formation of a base pair with cytosine at a specific position in the fragmented nucleic acid used is a single-stranded nucleic acid having a base sequence in which the point to form a base pair with the cytosine to be detected is adenine, cytosine, or thymine.

9. The method according to any one of 1 to 8, wherein the single-stranded nucleic acid having a base sequence capable of hybridizing to the fragmented nucleic acid but incapable of resulting in the formation of a base pair with cytosine at a specific position in the fragmented nucleic acid and a solid phase-binding site is added in an amount of 1 to 100 times, both inclusive, the concentration of the fragmented nucleic acid to be measured to form the double strand.

10. The method according to 1 to 9, wherein the base sequence of the single-stranded nucleic acid having a base sequence capable of hybridizing with the fragmented nucleic acid but incapable of resulting in the formation of a base pair with cytosine at a specific position in the fragmented nucleic acid and a solid phase-binding site is such a base sequence that a blunt end is formed in a double-stranded nucleic acid in forming the double strand with the nucleic acid to be measured fragmented by the restriction enzyme.

11. A kit for detecting methylcytosine in a nucleic acid sequence, comprising a combination of a restriction enzyme, a single-stranded nucleic acid having a base sequence capable of hybridizing with the fragmented nucleic acid to be measured but incapable of resulting in the formation of a base pair with cytosine at a specific position in the fragmented nucleic acid and biotin, an anti-methylcytosine antibody, and a solid-phased avidin.

Advantageous Effects of Invention

In the conventional method for determining whether or not the particular cytosine to be detected in a nucleic acid is methylated by placing the cytosine to be detected in a DNA bulge formed when the nucleic acid hybridizes to a complementary strand and measuring the amount of an antibody binding to the nucleic acid, it is difficult to selectively detect the methylation of the particular cytosine in DNA specimens, such as genomic DNA, to be actually analyzed because any methylcytosine mismatched with the complementary strand is recognized by an anti-methylcytosine antibody; the method has had poor industrial utility. The present invention has enabled the selective detection of the presence of the methylation of particular cytosine in the base sequence portion to be measured from a very long genome because it results in the base pair formation of any cytosine other than the cytosine to be detected with guanine, and thereby in no detection of methylcytosine to not be measured. This achieves greatly improved selectivity of the detection of the methylation of cytosine compared to that for the conventional methylcytosine detection technique using an anti-methylcytosine antibody.

BRIEF DESCRIPTION OF DRAWINGS

FIG. 6 is a graph showing the results of measuring the methylation rate of DNA by an enzyme immunoassay method in Example 3.

FIG. 7 is a graph showing the results of measuring a response when the amount of a complementary nucleic acid relative to the nucleic acid to be measured is changed by an enzyme immunoassay method in Example 4.

DESCRIPTION OF EMBODIMENTS

Figure 1:
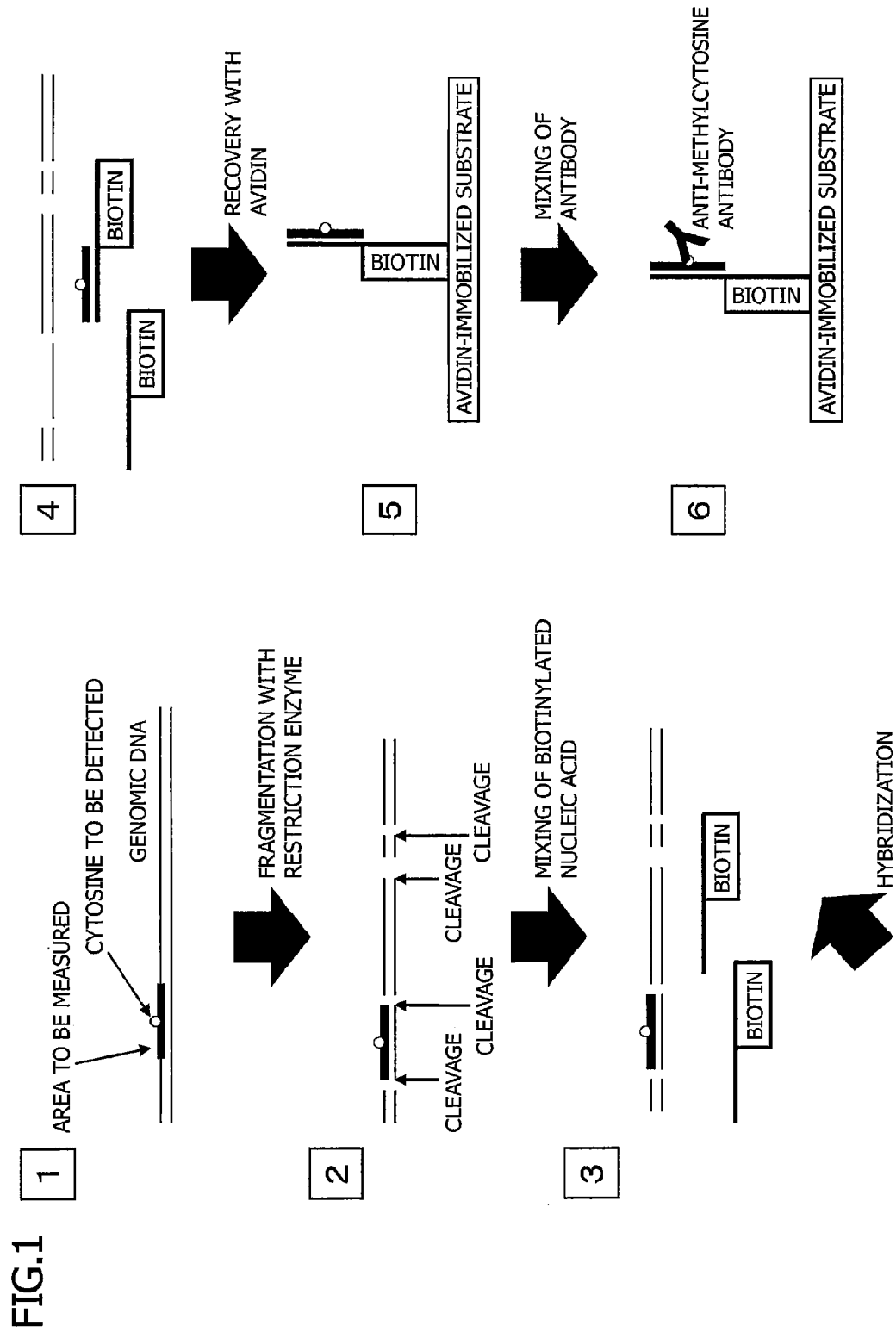
FIG. 1 is a schematic diagram showing the procedure of fragmenting a nucleic acid containing the area to be measured with a restriction enzyme, recovering the nucleic acid fragment of the area to be measured by hybridization to a biotinylated single-stranded nucleic acid, and detecting the particular cytosine to be detected with an anti-methylcytosine antibody, using the present invention.

The measurement procedure for the methylated state of cytosine at a specific position in a nucleic acid sequence according to the present invention is shown in FIG. 1.

According to the present invention, in selectively measuring only a nucleic acid having the base sequence to be measured (step 1 in FIG. 1) in a genome, the genomic DNA is first cleaved at any position with a restriction enzyme. The restriction enzyme used can be properly selected to suit the base sequence of the area to be measured. For example, AluI enzyme is known to recognize only 5'-AGCT-3' to cleave a nucleic acid between adjacent G and C bases. A restriction enzyme is used to prepare the fragment of the base sequence of the area to be measured (step 2 in FIG. 1). The base sequence of the area to be measured is determined by the selection of a restriction enzyme.

A biotinylated single-stranded nucleic acid is then added (step 3 in FIG. 1). Biotin is used as a solid phase-binding site. The base sequence of the biotinylated nucleic acid serves as a base sequence incapable of resulting in the formation of a base pair with the cytosine to be detected while having complementarity enabling the formation of a double strand with the nucleic acid of the area to be measured fragmented by the restriction enzyme. Examples of such a base sequence include a base sequence obtained by removing only guanine capable of forming a base pair with the cytosine to be detected from a base sequence as a completely complementary strand for the nucleic acid to be measured. In this case, the cytosine to be detected will be placed within a DNA bulge in the formed double-stranded DNA. The same is also possible by replacing guanine capable of forming a base pair with the cytosine to be detected in a completely complementary strand with cytosine, adenine, or thymine. In this case, the cytosine to be detected is in the state of being incapable of forming a base pair in the formed double-stranded DNA. Only the base moiety of guanine capable of forming a base pair with the cytosine to be detected in a completely complementary strand can also be removed to leave the deoxyribose to make an abasic site. Also in this case, the cytosine to be detected is in the state of being incapable of forming a base pair in the formed double-stranded DNA.

In addition, the base sequence of the biotinylated nucleic acid is preferably made in a state referred to as having a blunt end, in which an unpaired base is not present, by keeping the ends of both strands of a double-stranded nucleic acid aligned in forming a double strand with the nucleic acid to be measured. The blunt end can be obtained by matching the cleavage point for a restriction enzyme to the base sequence of the biotinylated single-stranded nucleic acid. The reason the blunt end is preferable is that the presence of methylcytosine as an outstanding unpaired base in the ends of both strands of the double-stranded nucleic acid results in the binding of the methylcytosine to the antibody and thus a methylation rate higher than an actual value. Even if an unpaired base is present in the ends of both strands of the double-stranded nucleic acid, the unpaired base being not methylcytosine is not directly a problem since it is not recognized by an anti-methylcytosine antibody. However, as described above, it is relatively easy to form a blunt end by the combination of a restriction enzyme and the base sequence of the biotinylated single-stranded nucleic acid; thus, an unpaired base is preferably absent in the ends of both strands of the double-stranded DNA.

Further, the biotinylated nucleic acid preferably has the same or higher concentration than that of the fragmented nucleic acid to be measured. This is for the purpose of decreasing the probability that the nucleic acid to be measured will hybridize again to the nucleic acid having originally formed a double strand. However, addition in large excess is not preferable because the rate of subsequent recovery on the solid phase is decreased. Thus, the amount of the biotinylated nucleic acid to be added is preferably on the order of 1 to 100 times that of the fragmented nucleic acid to be measured.

The nucleic acid to be measured is hybridized to the biotinylated single-stranded nucleic acid (step 4 in FIG. 1). The hybridization method involves once heating to the melting temperature (called Tm value) of the fragmented nucleic acid to be measured or higher, followed by slow cooling. In slow cooling, maintaining at around the Tm value for about 30 minutes improves the specificity of hybridization.

Thereafter, the nucleic acid to be measured hybridized to the biotinylated single-stranded nucleic acid is recovered using avidin-biotin binding (step 5 in FIG. 1). Biotin is known to firmly bind to avidin (and streptavidin). It is convenient for avidin to be immobilized on the solid phase surface in advance to suit a subsequent measurement method. For example, for the surface plasmon resonance method, avidin is immobilized on the gold thin film surface. For the enzyme immunoassay method, it is immobilized in the wells of a polystyrene or polyvinyl chloride microtiter plate. A method using avidin-immobilized magnetic beads is also widely known. As a method for immobilizing avidin, a heretofore known method can be widely used.

The nucleic acid mixture containing the biotinylated nucleic acid hybridized with the nucleic acid to be measured is introduced onto an avidin-immobilized substrate to selectively immobilize only the nucleic acid to be measured on the substrate by avidin-biotin binding. The substrate is then washed to remove the nucleic acid to not be measured which has not been hybridized with the biotinylated nucleic acid.

Thereafter, an anti-methylcytosine antibody is bound to the nucleic acid to be measured which is hybridized to the biotinylated nucleic acid and immobilized on the substrate (step 6 in FIG. 1). For the surface plasmon resonance method, a change in a refractive index due to the binding of antibody is observed; thus, the anti-methylcytosine antibody need not be labeled and can be detected on its own. In the enzyme immunoassay method, detection is carried out by labeling the anti-methylcytosine antibody with an enzyme, such as horseradish peroxidase, in advance, or using a secondary antibody method.

EXAMPLES

The present invention will now be more specifically described below based on Examples. However, the present invention is not intended to be limited to the Examples.

Example 1

This Example shows the experimental results of confirming that the present invention can measure methylcytosine in DNA by a surface plasmon resonance method.

The sensor chip used for surface plasmon resonance was prepared as follows by laminating a polydimethylsiloxane substrate on which a flow path was formed on a glass substrate having a gold thin film.

In preparing the polydimethylsiloxane substrate, an oligomer of polydimethylsiloxane (PDMS) (Corning Incorporated) and a hardener were mixed in a substrate providing a template for the flow path (3 mm in width, 10 mm in length, and 20 μm in depth), which was then allowed to stand at 60° C. for 2 hours for hardening. The resultant was then taken off the template to provide a PDMS substrate having the flow path.

Figure 2:
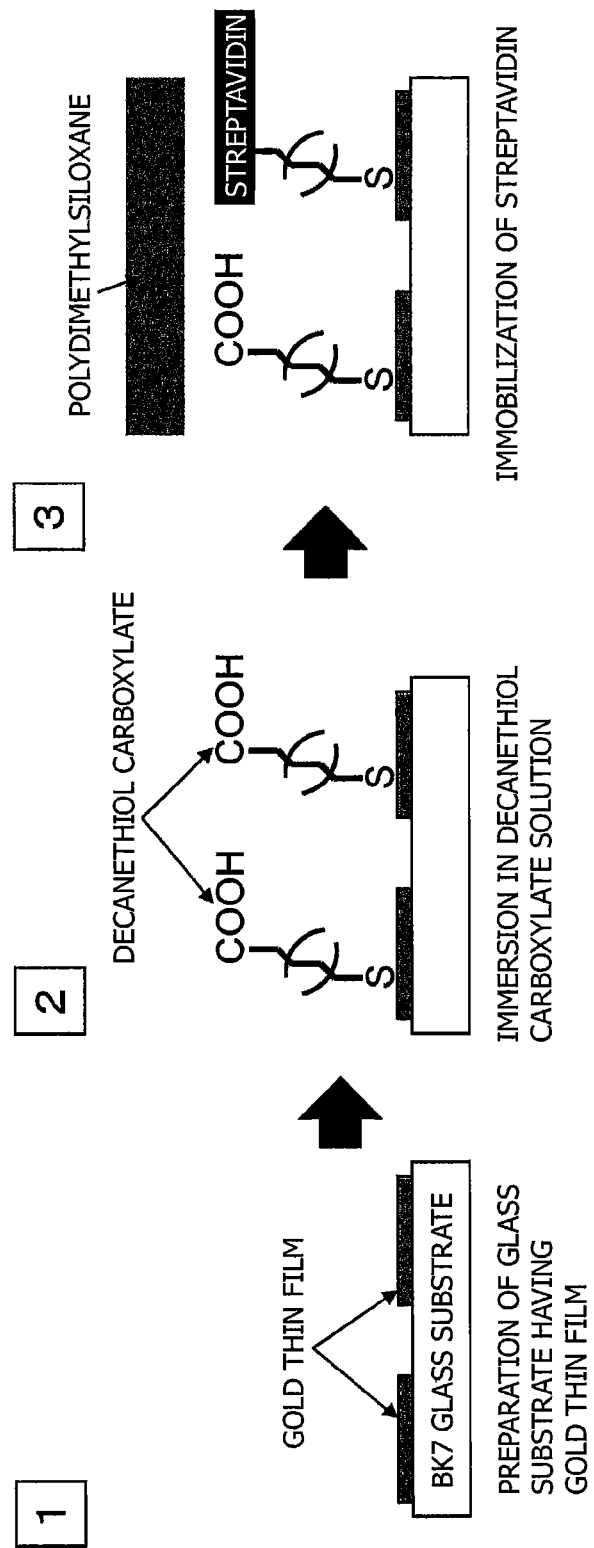
FIG. 2 is a schematic diagram showing the procedure of preparing a sensor when the measurement of antigen-antibody reaction in the present invention is carried out using a surface plasmon resonance method.

The glass substrate having a gold thin film was prepared as follows. A sticker perforated with 2 holes 3 mm in diameter was affixed to a BK7 glass substrate 18 mm square. Thereafter, using a magnetron sputtering system (Seed Lab., Corporation), titanium was deposited at 3 nm on the glass substrate and a gold thin film was further deposited at 50 nm thereon. The resultant was taken out of the magnetron sputtering system, followed by peeling off the sticker to prepare a glass substrate having 2 gold thin films 3 mm in diameter (step 1 in FIG. 2).

The immobilization of avidin on the gold thin film surface was performed as follows. Decanethiol carboxylate was dissolved in ethanol to prepare a 1 mM solution. The glass substrate having a gold thin film was immersed in the solution overnight to modify the gold surface with decanethiol carboxylate by gold-thiol binding (step 2 in FIG. 2). Then, 5 μL of MES buffer containing 5 mM N-hydroxysulfosuccinimide and 40 mM N,N'-diisopropylcarbodiimide (pH 6.0) were added dropwise to only one of the gold thin films, which was then reacted at room temperature for 30 minutes to activate the carboxyl group of decanethiol carboxylate. The gold thin film was subsequently washed with pure water and reacted with 0.1 mg/mL streptavidin (diluted with phosphate buffer (pH 7.4)) at room temperature for 2 hours (step 3 in FIG. 2). After washing with pure water, the resultant was reacted with 1 M ethanolamine (diluted with phosphate buffered saline (pH 7.4)) at room temperature for 15 minutes for inactivation and was then washed with pure water. Finally, the polydimethylsiloxane substrate on which a flow path was formed was laminated on the glass substrate having a gold thin film to make a sensor.

The fragmented methylated genomic DNA specimen was prepared as follows. λDNA (Takara Bio Inc., code No. 3010, about 48,000 bp) was used. 40 μL of λDNA (stock solution: 0.34 μg/μL) was taken, and 10 μL of AluI (Takara Bio Inc.) as a restriction enzyme and 50 μL of 10× buffer provided with the restriction enzyme were placed therein. The mixture was then reacted at 37° C. for 4 hours to fragment λDNA. Thereafter, 2 μL (8 units) of an enzyme methylating cytosine located at the CpG regions (M. SssI, New England Biolabs Inc.) and 10 μL of S-adenosylmethionine (stock solution: 32 mM) were placed therein, which was then reacted overnight. The λDNA treated with the enzyme was handled as DNA methylated in the CpG regions. The sequence of the DNA is 5'-CTTTCCCGGAATTACGCCCAGATGAG-3' (C at the 15th base from the 5'-end is methylcytosine) (SEQ ID NO: 1). Using combined bisulfite restriction analysis (COBRA method) as a conventional method, it was confirmed that 99% or more of the CpG regions to be measured were methylated.

Using Unmethylated λDNA (Promega KK., catalog No. D1521) as λDNA not methylated in CpG, a fragmented specimen was similarly prepared. This λDNA lacks dam and dcm methylase activities and is on the market as one containing no methylcytosine.

The present inventors have also confirmed by the COBRA method that 1% or less of the CpG regions to be measured were methylated in the fragmented DNA prepared using this λDNA.

Measurement was carried out as follows. A surface plasmon resonance sensor (NTT Advance Technology Corporation) was equipped with the sensor chip prepared above through matching oil. A specimen was then introduced into the sensor using a syringe pump (CMA Corporation). Phosphate buffer (containing 0.1% bovine serum albumin and 0.05% Tween 20) was used for this measurement. First, the fragmented λDNA to be measured and a biotinylated nucleic acid were mixed to a final concentration of 935 pM. The base sequence of the biotinylated nucleic acid used in this Example was 5'-CTCATCTGGGCTAATTCCGGGAA AG-3' (SEQ ID NO: 2), was a sequence completely complementary to the sequence of the DNA to be measured except for the absence of a base corresponding to C at the 15th base from the 5'-end of the sequence of the DNA to be measured, and had biotin at the 5'-end. The mixture was heated at 95° C. for 5 minutes and then slowly cooled to room temperature (step 1 in FIG. 3).

Figure 3:
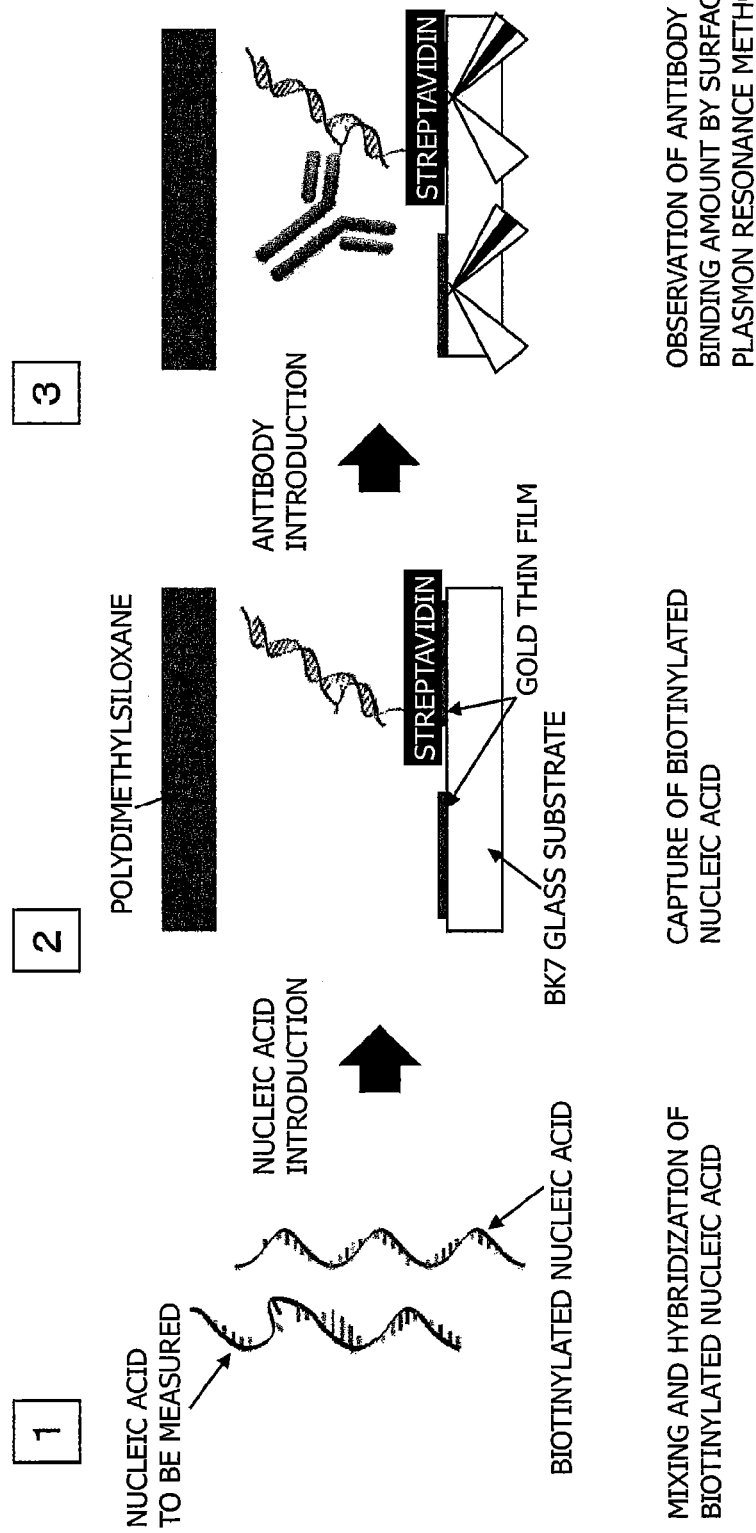
FIG. 3 is a schematic diagram showing the procedure of measurement when the measurement of antigen-antibody reaction in the present invention is carried out using a surface plasmon resonance method.

Ten-fold dilution series were prepared using phosphate buffer, and the diluted specimens were each introduced at a flow rate of 2 μL/minute for 30 minutes to capture the biotinylated nucleic acid with streptavidin in the sensor (step 2 in FIG. 3). Streptavidin can be immobilized in only one sensor to capture the biotinylated nucleic acid only by the streptavidin-immobilized gold thin film surface.

Phosphate buffer (containing 0.1% bovine serum albumin and 0.05% Tween 20) was introduced as a running buffer into the sensor for 15 minutes for washing to stabilize the response of the sensor, followed by introducing 10 μg/mL of an anti-methylcytosine antibody (Aviva Systems Biology Corporation) to observe the amount of the antibody binding to the biotinylated nucleic acid captured in the sensor as a change in the surface plasmon resonance angle. Since streptavidin was immobilized in one of the sensors, the change in the surface plasmon resonance angle on the gold thin film surface on which streptavidin was not immobilized can be thought as the nonspecific adsorption amount of other than the nucleic acid to be measured. The surface on which streptavidin is not immobilized is not essential; however, the use of this surface enables easy estimation in measuring the nonspecific adsorption amount.

Figure 4:
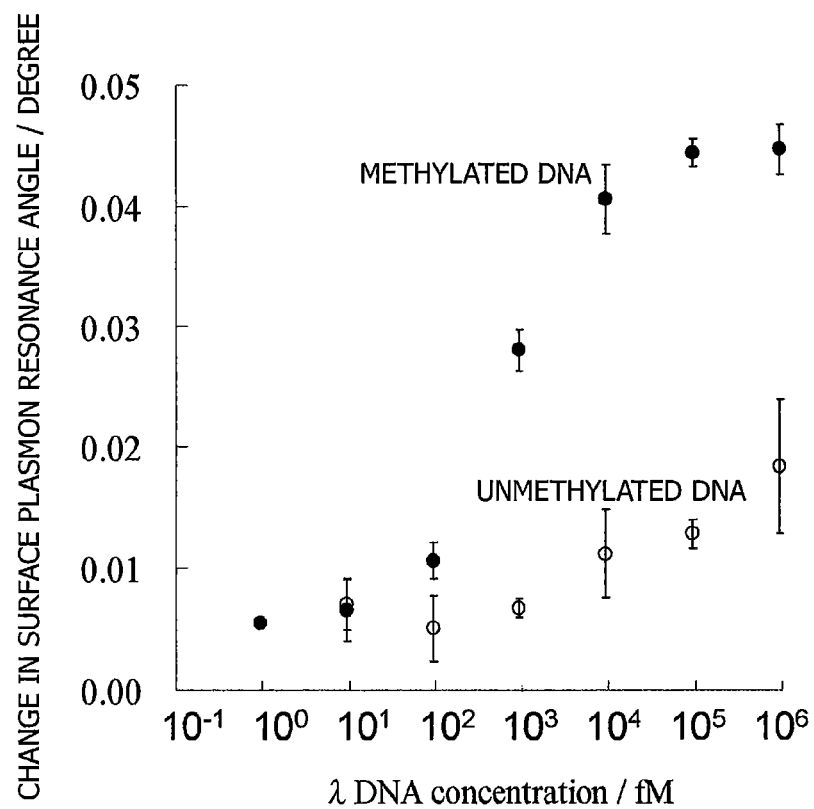
FIG. 4 is a graph comparing the results of measuring the surface plasmon resonance angle for methylated DNA and unmethylated DNA in Example 1.

The measurement results are shown in FIG. 4. For λDNA in which the CpG regions are methylated, the amount of change in the surface plasmon resonance angle was shown to increase with increasing specimen concentration. However, the change in the surface plasmon resonance angle was small for the unmethylated DNA. These are because the introduction of the anti-methylcytosine antibody resulted in the binding of the anti-methylcytosine antibody to methylated cytosine in the nucleic acid to be measured hybridized to the biotinylated nucleic acid, increasing the refractive index of the gold thin film surface. Thus, the method of the present invention can measure whether or not cytosine in genomic DNA has been methylated.

Example 2

This Example shows that it is suitable for the biotinylated nucleic acid used in the present invention to be made in a base sequence not forming a base pair with the cytosine to be detected.

DNA was prepared as follows. The nucleic acid to be measured used was 5'-TTG CGC GGC GTC CGT CCT GTT GAC TTC-3 (C at the 13th base from the 5'-end is methylcytosine) (SEQ ID NO: 3). The nucleic acid to be measured was hybridized to each of the following 6 biotinylated nucleic acids by the same procedure as in Example 1.

5'-GAA GTC AAC AGG AC_ GAC GCC GCG CAA-3' (SEQ ID NO: 4) is designed so that the cytosine to be detected is placed in the bulge.

5'-GAA GTC AAC AGG ACA GAC GCC GCG CAA-3' (SEQ ID NO: 5) has a mismatch in which the base to form a base pair with the cytosine to be detected is A.

5'-GAA GTC AAC AGG ACT GAC GCC GCG CAA-3' (SEQ ID NO: 6) has a mismatch in which the base to form a base pair with the cytosine to be detected is T.

5'-GAA GTC AAC AGO ACC GAC GCC GCG CAA-3' (SEQ ID NO: 7) has a mismatch in which the base to form a base pair with the cytosine to be detected is C.

5'-GAA GTC AAC AGG ACd GAC GCC GCG CAA-3' (SEQ ID NO: 8) has a mismatch in which the base to form a base pair with the cytosine to be detected is an abasic site (called an AP site).

5'-GAA GTC AAC AGG ACG GAC GCC GCG CAA-3' (SEQ ID NO: 9) is a completely complementary strand in which the base to form a base pair with the cytosine to be detected is G.

In this Example, the surface plasmon resonance measuring instrument used was a sensor chip in which Biacore T100 (GE Healthcare) and streptavidin are immobilized (Sensor chip SA, GE Healthcare).

First, 1 nM DNA forming a double strand was fed to the sensor chip at 10 μL/minute for 30 minutes for capture on the sensor surface. Then, various concentrations (0.25, 0.5, 1, 2.5, 5, 10, 25, and 50 nM) of an anti-methylcytosine antibody were fed at 10 μL/minute for 10 minutes. As a running buffer, HBS-EP buffer (pH 7.4, containing 10 mM HEPES, 0.15 M NaCl, 3 mM EDTA, and 0.05% v/v Surfactant P20) from GE Healthcare was used. Then, a buffer containing no antibody was fed at 10 μL/minute for 5 minutes. Thereafter, as a regeneration solution, 50 mM Gly-NaOH (pH 10.6) was fed at 60 μL/minute for 30 seconds. Under the conditions of this regeneration solution, it has been confirmed that the antigen-antibody reaction is dissociated while the double strand of DNA is maintained, enabling the antibody to be repeatedly fed.

Figure 5:
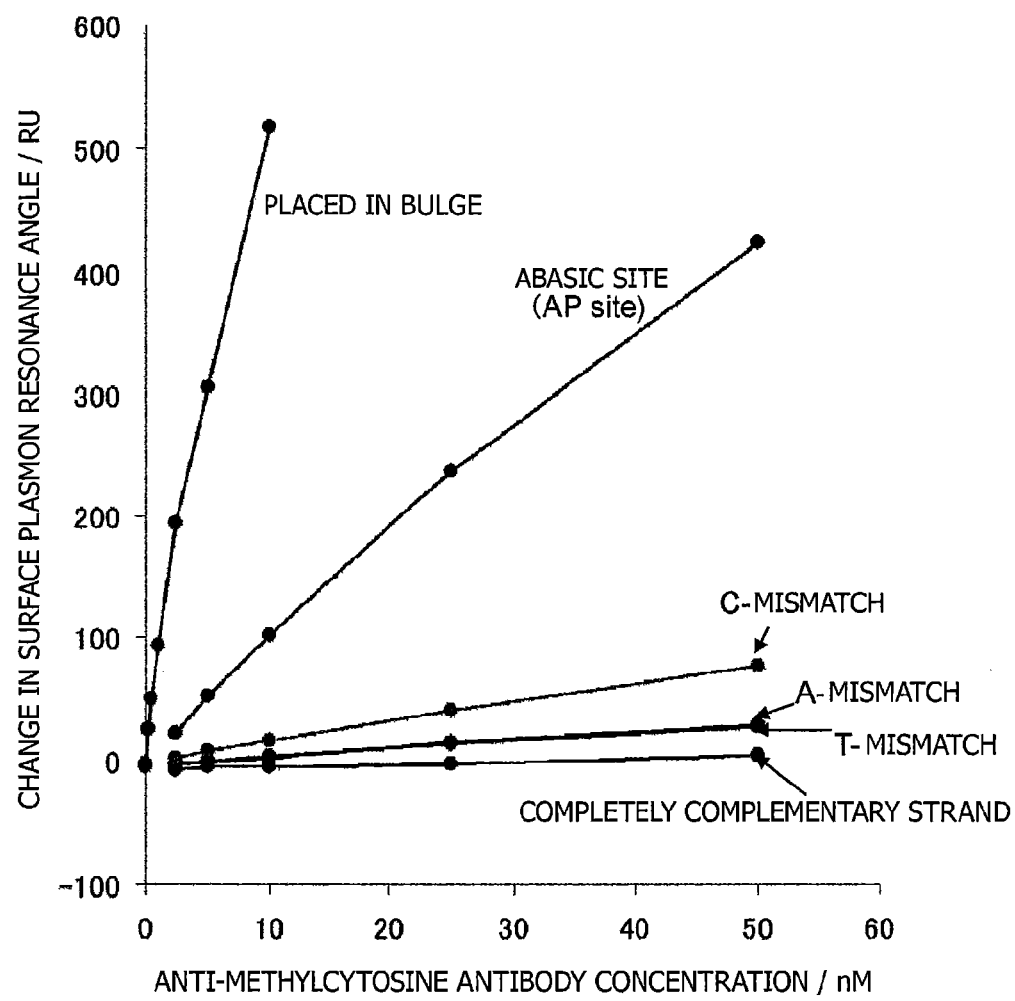
FIG. 5 is a graph comparing the results of measuring the surface plasmon resonance angle for methylcytosine using various complementary nucleic acids in Example 2.

The measurement results are shown in FIG. 5. The largest response was obtained when methylcytosine was placed in the bulge. A large response was also obtained when the point to form a base pair with methylcytosine is an abasic site (called an AP site). In contrast to these cases, no binding of the anti-methylcytosine antibody was observed to the completely complementary double strand. It was shown that a slight response could also be obtained when the point to form a base pair with methylcytosine was adenine, cytosine, or thymine and these are also applicable for the present invention.

The results of this Example clearly show that it is necessary for the base sequence of the biotinylated nucleic acid used in the present invention to have a base sequence in which a base pair is not formed with the.

Example 3

This Example shows the experimental results of confirming that the method of the present invention can measure the rate of cytosine methylation in DNA by an enzyme immunoassay method.

The DNA to be measured used was fragmented λDNA. The DNA specimen, in which all CpG regions were methylated, was prepared by methylation with an enzyme as in Example 1. The DNA specimen, in which all CpG regions are not methylated, that was used was fragmented unmethylated λDNA (Promega KK., catalog No. D1521) as in Example 1. These specimens were mixed to prepare a DNA specimen sample having a methylation rate of 0, 25, 50, 75, or 100%. The resultant DNAs were each mixed with the same biotinylated nucleic acid as that in Example 1, heated at 95° C. for 5 minutes, and then slowly cooled to room temperature.

The enzyme immunoassay method was performed as follows. A streptavidin-coated plate (Sumitomo Bakelite Co., Ltd.) was provided, and 200 μL each of the DNA specimens were introduced into its wells. Washing was carried out with 300 μL of a buffer (containing phosphate buffered saline, pH 7.4, and 0.05% Tween 20) 3 times, followed by adding 50 μL of 1 μg/mL of a horseradish peroxidase-labeled anti-methylcytosine antibody to each well and conducting reaction at 37° for 30 minutes under seal. Washing was carried out with 300 μL of the buffer 4 times, followed by adding 50 μL of a tetramethylbenzidine solution (Bethyl Laboratories Inc.) and conducting reaction for 10 minutes under light-shielding. A 2N hydrochloric acid solution (50 μL) was added to stop the reaction, and absorbance at 450 nm was measured using a microplate reader (BioRad model 680).

The measurement results are shown in FIG. 6. The absorbance was confirmed to increase with increasing methylation rate. From this, it was found that the present invention enabled the measurement of the rate of cytosine methylation in DNA by an enzyme immunoassay method.

Example 4

This Example shows that it is suitable for a biotinylated single-stranded nucleic acid to be added in an amount of 1 to 100 times, both inclusive, the concentration of the nucleic acid fragment to be measured in the method of the present invention.

The DNA to be measured used was 5'-CTTTCCCG-GAATTACGCCCAGATGAG-3' (C at the 15th base from the 5'-end is methylcytosine) (SEQ ID NO: 1). The object to be measured and DNA (5'-CTCATCTGGGCGTAATTC-CGGGAAAG-3') (SEQ ID NO: 10) as a completely complementary strand were mixed at the same concentration (1 nM), heated at 95° C. for 5 minutes, and then slowly cooled to room temperature to form a completely complementary double strand. A biotinylated nucleic acid (5'-(biotin)CT-CATCTGGGCTAATTCCGGGAA AG-3', the absence of a complementary base G corresponding to C at the 15th base from the 5'-end of the DNA to be measured (SEQ ID NO: 2)) was added to a final concentration of 0, 0.5, 1, 5, 10, 50, or 100 nM to the double-stranded DNA, which was then again heated at 95° C. for 5 minutes and then slowly cooled to room temperature to hybridize the biotinylated nucleic acid to the DNA to be measured having methylcytosine. Thereafter, measurement was carried out by the enzyme immunoassay method as in Example 3.

The measurement results are shown in FIG. 7. A larger response was obtained by increasing the amount of the biotinylated nucleic acid relative to that of the nucleic acid to be measured. This is because of an increase in the proportion of the nucleic acid to be measured hybridized with the biotinylated nucleic acid. However, an amount in extreme excess decreases the response because it decreases the recovery rate of the biotinylated nucleic acid. Under the present conditions, the concentration of the same to on the order of 100 times that of the nucleic acid to be measured was shown to be satisfactory.

---

The invention claimed is:

1. A method for detecting the methylated state of cytosine at a specific position contained in a nucleic acid, comprising the steps of:
   fragmenting the nucleic acid using a restriction enzyme;
   forming a double-stranded nucleic acid between the fragmented nucleic acid and a single-stranded nucleic acid having a base sequence capable of hybridizing with the fragmented nucleic acid but incapable of resulting in the formation of a base pair with cytosine at the specific position in the fragmented nucleic acid and a solid phase-binding site;
   binding the double-stranded nucleic acid on a solid phase using the solid phase-binding site; and
   measuring the amount of an anti-methylcytosine antibody binding to the double-stranded nucleic acid on the solid phase by detecting the binding of the antibody using a surface plasmon resonance method.

2. The method according to claim 1, wherein the solid phase-binding site is biotin and avidin is immobilized on the solid phase.

3. The method according to claim 1, wherein the base sequence capable of hybridizing to the fragmented nucleic acid but incapable of resulting in the formation of a base pair with cytosine at a specific position in the fragmented nucleic acid used is a single-stranded nucleic acid having a base sequence in which the point to form a base pair with the cytosine to be detected is an abasic site.

4. The method according to claim 1, wherein the base sequence capable of hybridizing with the fragmented nucleic acid but incapable of resulting in the formation of the base pair with cytosine at the specific position in the fragmented nucleic acid used is a single-stranded nucleic acid having a base sequence in which the cytosine to be detected is to be placed in a bulge structure in forming the double-stranded nucleic acid.

5. The method according to claim 1, wherein the base sequence capable of hybridizing with the fragmented nucleic acid but incapable of resulting in the formation of a base pair with cytosine at a specific position in the fragmented nucleic acid used is a single-stranded nucleic acid having a base sequence in which the point to form a base pair with the cytosine to be detected is adenine, cytosine, or thymine.

6. The method according to claim 1, wherein the single-stranded nucleic acid is added in an amount of 1 to 100 times, both inclusive, the concentration of the fragmented nucleic acid to be measured to form the double strand.

7. The method according to claim 1, wherein the single-stranded nucleic acid has a base sequence that forms a blunt end when a double-stranded nucleic acid is formed with the fragmented nucleic acid.

8. The method according to claim 1, wherein the nucleic acid to be fragmented is a genomic nucleic acid.

9. The method according to claim 1, wherein the concentration of the double-stranded nucleic acid at the step of forming the double-stranded nucleic acid is $1\times10^2$ to $1\times10^6$ fM.

* * * * *

UNITED STATES PATENT AND TRADEMARK OFFICE
CERTIFICATE OF CORRECTION

PATENT NO. : 9,988,672 B2  
APPLICATION NO. : 14/775004  
DATED : June 5, 2018  
INVENTOR(S) : Kurita et al.

Page 1 of 1

It is certified that error appears in the above-identified patent and that said Letters Patent is hereby corrected as shown below:

In the Specification

Column 10, Line 27: Please correct "ACA" to read -- AC<u>A</u> --

Column 10, Line 30: Please correct "ACT" to read -- AC<u>T</u> --

Column 10, Line 33: Please correct "AGO" to read -- AGG --

Column 10, Line 33: Please correct "ACC" to read -- AC<u>C</u> --

Column 10, Line 36: Please correct "ACd" to read -- AC<u>d</u> --

Column 10, Line 40: Please correct "ACG" to read -- AC<u>G</u> --

Column 11, Line 18: Please correct "ADNA" to read -- λDNA --

Signed and Sealed this  
Twenty-eighth Day of August, 2018

Andrei Iancu  
*Director of the United States Patent and Trademark Office*

SEQUENCE LISTING

<160> NUMBER OF SEQ ID NOS: 10

<210> SEQ ID NO 1
<211> LENGTH: 26
<212> TYPE: DNA
<213> ORGANISM: Artificial
<220> FEATURE:
<223> OTHER INFORMATION: Target
<220> FEATURE:
<221> NAME/KEY: modified_base
<222> LOCATION: (15)..(15)
<223> OTHER INFORMATION: m5c

<400> SEQUENCE: 1
ctttcccgga attacgccca gatgag       26

<210> SEQ ID NO 2
<211> LENGTH: 25
<212> TYPE: DNA

```
<213> ORGANISM: Artificial
<220> FEATURE:
<223> OTHER INFORMATION: Probe

<400> SEQUENCE: 2
ctcatctggg ctaattccgg gaaag                                              25

<210> SEQ ID NO 3
<211> LENGTH: 27
<212> TYPE: DNA
<213> ORGANISM: Artificial
<220> FEATURE:
<223> OTHER INFORMATION: Target
<220> FEATURE:
<221> NAME/KEY: modified_base
<222> LOCATION: (13)..(13)
<223> OTHER INFORMATION: m5c

<400> SEQUENCE: 3
ttgcgcggcg tccgtcctgt tgacttc                                            27

<210> SEQ ID NO 4
<211> LENGTH: 26
<212> TYPE: DNA
<213> ORGANISM: Artificial
<220> FEATURE:
<223> OTHER INFORMATION: Probe

<400> SEQUENCE: 4
gaagtcaaca ggacgacgcc gcgcaa                                             26

<210> SEQ ID NO 5
<211> LENGTH: 27
<212> TYPE: DNA
<213> ORGANISM: Artificial
<220> FEATURE:
<223> OTHER INFORMATION: Probe

<400> SEQUENCE: 5
gaagtcaaca ggacagacgc cgcgcaa                                            27

<210> SEQ ID NO 6
<211> LENGTH: 27
<212> TYPE: DNA
<213> ORGANISM: Artificial
<220> FEATURE:
<223> OTHER INFORMATION: Probe

<400> SEQUENCE: 6
gaagtcaaca ggactgacgc cgcgcaa                                            27

<210> SEQ ID NO 7
<211> LENGTH: 27
<212> TYPE: DNA
<213> ORGANISM: Artificial
<220> FEATURE:
<223> OTHER INFORMATION: Probe

<400> SEQUENCE: 7
gaagtcaaca ggaccgacgc cgcgcaa                                            27

<210> SEQ ID NO 8
<211> LENGTH: 27
<212> TYPE: DNA
<213> ORGANISM: Artificial
<220> FEATURE:
<223> OTHER INFORMATION: Probe
```

```
<220> FEATURE:
<221> NAME/KEY: modified_base
<222> LOCATION: (15)..(15)
<223> OTHER INFORMATION: AP site
<220> FEATURE:
<221> NAME/KEY: misc_feature
<222> LOCATION: (15)..(15)
<223> OTHER INFORMATION: n is a, c, g, or t

<400> SEQUENCE: 8
gaagtcaaca ggacngacgc cgcgcaa                                             27

<210> SEQ ID NO 9
<211> LENGTH: 27
<212> TYPE: DNA
<213> ORGANISM: Artificial
<220> FEATURE:
<223> OTHER INFORMATION: Probe

<400> SEQUENCE: 9
gaagtcaaca ggacggacgc cgcgcaa                                             27

<210> SEQ ID NO 10
<211> LENGTH: 26
<212> TYPE: DNA
<213> ORGANISM: Artificial
<220> FEATURE:
<223> OTHER INFORMATION: Complementary sequence of target

<400> SEQUENCE: 10
ctcatctggg cgtaattccg ggaaag                                              26
```